United States Patent
Becker

(10) Patent No.: US 9,476,025 B2
(45) Date of Patent: Oct. 25, 2016

(54) FERROMAGNETIC CELL AND TISSUE CULTURE MICROCARRIERS

(71) Applicant: University of South Florida, Tampa, FL (US)

(72) Inventor: Jeanne L. Becker, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/459,668

(22) Filed: Aug. 14, 2014

(65) Prior Publication Data

US 2014/0356955 A1    Dec. 4, 2014

Related U.S. Application Data

(63) Continuation of application No. 14/090,655, filed on Nov. 26, 2013, now abandoned, which is a continuation of application No. 11/307,077, filed on Jan. 23, 2006, now abandoned, which is a continuation of application No. PCT/US2004/023746, filed on Jul. 23, 2004.

(60) Provisional application No. 60/481,126, filed on Jul. 23, 2003.

(51) Int. Cl.
| | |
|---|---|
| *C12N 5/00* | (2006.01) |
| *C12N 11/02* | (2006.01) |
| *C12N 13/00* | (2006.01) |
| *C12N 5/071* | (2010.01) |

(52) U.S. Cl.
CPC ............ *C12N 5/0075* (2013.01); *C12N 5/0602* (2013.01); *C12N 11/02* (2013.01); *C12N 13/00* (2013.01); *C12N 2513/00* (2013.01); *C12N 2529/00* (2013.01); *C12N 2531/00* (2013.01); *C12N 2533/10* (2013.01); *C12N 2533/54* (2013.01); *C12N 2533/74* (2013.01)

(58) Field of Classification Search
None
See application file for complete search history.

(56) References Cited

U.S. PATENT DOCUMENTS

| | | |
|---|---|---|
| 4,687,748 A | 8/1987 | Schroder |
| 4,897,444 A | 1/1990 | Brynes et al. |
| 4,959,301 A | 9/1990 | Weaver et al. |
| 4,988,623 A | 1/1991 | Schwarz et al. |
| 4,994,388 A | 2/1991 | Hillegas et al. |
| 5,026,650 A | 6/1991 | Schwarz et al. |
| 5,100,799 A | 3/1992 | Mundt |
| 5,153,131 A | 10/1992 | Wolf et al. |
| 5,225,332 A | 7/1993 | Weaver et al. |
| 5,269,745 A | 12/1993 | Liboff et al. |
| 5,396,136 A | 3/1995 | Pelrine |
| 5,427,935 A | 6/1995 | Wang et al. |
| 5,458,558 A | 10/1995 | Liboff et al. |
| 5,496,722 A * | 3/1996 | Goodwin .............. C12M 23/24 435/1.1 |
| 5,612,188 A | 3/1997 | Shuler et al. |
| 5,935,849 A | 8/1999 | Schinstine et al. |
| 5,989,913 A | 11/1999 | Anderson et al. |
| 6,054,319 A | 4/2000 | Worden et al. |
| 6,080,581 A | 6/2000 | Anderson et al. |
| 6,203,487 B1 | 3/2001 | Consigny |
| 6,326,203 B1 | 12/2001 | Worden et al. |
| 6,383,470 B1 | 5/2002 | Fritzsch et al. |
| 6,455,310 B1 | 9/2002 | Barbera-Guillem |
| 6,485,963 B1 | 11/2002 | Wolf et al. |
| 6,673,597 B2 | 1/2004 | Wolf et al. |
| 2002/0106314 A1* | 8/2002 | Pelrine ................. B01J 19/0046 422/186 |
| 2003/0059764 A1 | 3/2003 | Ravkin et al. |
| 2003/0077225 A1 | 4/2003 | Laurent et al. |
| 2004/0058408 A1 | 3/2004 | Thomas et al. |
| 2004/0208761 A1 | 10/2004 | Bader |
| 2005/0054101 A1 | 3/2005 | Felder et al. |
| 2005/0255583 A1 | 11/2005 | DePaola et al. |
| 2006/0199170 A1 | 9/2006 | Becker |
| 2009/0137018 A1 | 5/2009 | Becker et al. |
| 2014/0087440 A1 | 3/2014 | Becker et al. |
| 2014/0087467 A1 | 3/2014 | Becker |

FOREIGN PATENT DOCUMENTS

| | | |
|---|---|---|
| CA | 1307225 C | 9/1992 |
| CN | 1289842 A | 4/2001 |
| WO | WO 82/00660 A1 | 3/1982 |
| WO | WO 01/81460 A1 | 11/2001 |
| WO | WO 02/33419 A1 | 4/2002 |
| WO | WO 02/051985 A2 | 7/2002 |
| WO | WO 2005/003332 A2 | 1/2005 |

(Continued)

OTHER PUBLICATIONS

International Search Report and Written Opinion mailed Jul. 1, 2005 for Application No. PCT/US2004/020908.
International Preliminary Report on Patentability mailed Jan. 3, 2006 for Application No. PCT/US2004/020908.
[No Author Listed], Collagen from human placenta. Product No. C7521. Sigma-Aldrich. Updated May 2006. 1 page.
[No Author Listed], Diamagnetic Levitation. www.physics.ucla.edu/marty/diamag/index.html [last accessed Oct. 24, 2014]. 3 pages.
[No Author Listed], Diamagnetically stabilised levitation. Aug. 16, 1999. XP002331831. http://www.hfml.ru.nl/fingertip.html [last accessed Dec. 5, 2014]. 2 pages.

(Continued)

*Primary Examiner* — Emily Cordas
(74) *Attorney, Agent, or Firm* — Wolf, Greenfield & Sacks, P.C.

(57) ABSTRACT

A porous, collagen coated, ferromagnetic cell culture microcarrier, which is suitable for in vitro cell and tissue culture and which facilitates 3D multicellular construct generation. Also provided is a method for creating batches of microcarriers which have inserted within them magnetite (Fe3O4) in the presence of collagen, thus creating a microcarrier which becomes magnetic in nature when placed in a the presence of a magnetic field and which facilitates cellular adherence (via the collagen coating) for 3D construct development.

23 Claims, 4 Drawing Sheets

(56) References Cited

FOREIGN PATENT DOCUMENTS

| | | |
|---|---|---|
| WO | WO 2005/010139 | 2/2005 |
| WO | WO 2005/010139 A2 | 2/2005 |

OTHER PUBLICATIONS

[No Author Listed], Microarray. Dec. 8, 1998 http://www.tmc.tulane.edu/astrobiology/microarray/default.html_1998. [last accessed Mar. 29, 2006]. 2 pages.

[No Author Listed], Phagocyte. Wikipedia. http://en.wikipedia.org/wiki/Phagocyte [last accessed Feb. 10, 2009]. 19 pages.

[No Author Listed], Rotate. Merriam-Webster Online. www.merriam-webster.com/dictionary/rotate [last accessed Feb. 10, 2009]. 2 pages.

[No Author Listed], Stir. Merriam-Webster Online, www.merriam-webster.com/dictionary/stir [last accessed Feb. 10, 2009]. 3 pages.

[No Author Listed], The Scientist 2009 Top 10 Innovations. The Scientist Magazine. Dec. 1, 2009. www.the-scientist.com/article/print/56171. 9 pages.

[No Author Listed], Welcome to the Larry the Frog Magnetic Levitation Movie Theater . . . May 12, 2001. http://pub26.bravenet.com/forum/static/show.php?usernum=2207974340&frmid=3071&msgid=104756&cmd=show [last accessed Dec. 2, 2014]. 3 pages.

Altankov et al., Synthesis of protein-coated gelatin microspheres and their use as microcarriers for cell culture. Part I. Derivatization with native collagen. J Biomater Sci Polym Ed. 1991;2(2):81-9.

Becker et at, Three-Dimensional Growth and Differentiation of Ovarian Tumor Cell Line in High Aspect Rotating-Wall Vessel: Morphologic and Embryologic Considerations. J Cell Biochem. 1993;51:283-9.

Carmeliet et al., Microgravity Reduces the Differentiation of Human Osteoblastic MG-63 Cells. National Library of Medicine. J Bone Miner Res. May 1997;12(5):786-94.

Carrière et al., Whole blood capcellia CD4/CD8 immunoassay for enumeration of CD4+ and CD8+ peripheral T lymphocytes. Clin Chem. Jan. 1999;45(1):92-7.

Cartmell et al., Preliminary analysis of magnetic particle techniques for activating mechanotransduction in bone cells. IEEE. 2002;87-8.

Chang et al., Stabilization of tetanus toxoid in poly(DL-lactic-co-glycolic acid) microspheres for the controlled release of antigen. J Pharm Sci. Feb. 1996;85(2):129-32.

Dandagi et al., Mucoadhesive Microspheres of Propranodol Hydrochloride for Nasal Delivery. Indian J Pharm Sci. 2007;69(3):402-7.

Emerich et al., Application of polymer-encapsulated cell therapy for CNS diseases. Neuromethods. 2000;36:233-77.

Geim et al., Magnet levitation at Your Fingertips. Nature. Jul. 22, 1999;400:323-4.

Geim, Everyone's Magnetism. Physics Today. Sep. 1998:36-9.

Glogauer et al., A new method for application of force to cells via ferric oxide beads. Pflugers Arch. Jan. 1998;435(2):320-7. Review.

Glogauer et al., Magnetic fields applied to collagen-coated ferric oxide beads induce stretch-activated Ca2+ flux in fibroblasts. Am J Physiol. Nov. 1998;269(5 Pt 1):C1093-104.

Goodwin et al., Three-Dimensional Culture of a Mixed Mullerian Tumor of the Ovary: Expression of In Vivo Characteristics. In Vitro Cell Dev Biol—Animal. May 1997;33:366-74.

Hammond et al., Mechanical Culture Conditions Effect Gene Expression; Gravity-Induced Changes on the Space Shuttle. Physiol Genomics. 2000;3(3):163-73. Epub Sep. 8, 2000. 15 pages.

Hammond et al., Optimized suspension culture: the rotating-wall vessel. Am J Physiol Renal Physiol. Jul. 2001;281(1):F12-25.

HFML University of Nijmegen, Levitation. www.hfml.kun.nl/fingertip.html [last accessed Mar. 29, 2006]. 2 pages.

HFML University of Nijmegen, The Real Levitation. www.hfml.sci.kun.nl/levitate.html [last accessed Apr. 7, 2003]. 2 pages.

Hopkin, Magnet-making bacteria could target tumors. Nature. Sep. 8, 2004. doi:10.1038/news040906-11. www.nature.com/news/2004/040906/full/040906-11.html. [Last accessed Oct. 6, 2004] 3 pages.

Johanson et al. *Saccharomyces cerevisiae* Gen Expression Changes During Rotating Wall Vessel Suspension Culture. J Appl Physiol. 2002;93:2171-80.

Kato et al., Immobilized culture of nonadherent cells on an oleyl poly(ethylene glycol) ethermodified surface. BioTechniques. 2003;35:1014-21.

Knowles et al., Mechanism of collagen phagocytosis by human gingival fibroblasts: importance of collagen structure in cell recognition and internalization. J Cell Sci. Apr. 1991;98 ( Pt 4):551-8.

Krombach et al., Cell size of alveolar macrophages: an interspecies comparison. Environ Health Perspect. Sep. 1997;105 Suppl 5:1261-3.

Kwon et al., Calcium-alginate gel bead cross-linked with gelatin as microcarrier for anchorage-dependent cell culture. BioTechniques. 2002;33:212-8.

Leach et al., Encapsulation of protein nanoparticles into uniform-sized microspheres formed in a spinning oil film. AAPS PharmSciTech. Dec. 6, 2005;6(4):E605-17.

Levine et al., Optimization of growth surface parameters in microcarrier cell culture. Biotechnol Bioengineering. 1979;21(5):821-45.

Lewis et al., cDNA Microarray Reveals Altered Cytosleletal Gene Expression in Space-Flown Leukemic T Lymphocytes (Jurkat). FASEB J. Aug. 2001;15:1783-5.

Lo et al., Cell-substrate separation: effect of applied force and temperature. Eur Biophys J. 1998;27(1):9-17.

Mathew, A study of the fluid mechanics and the cultivation of mammalian cells in a magnetically stabilized fluidized bed bioreactor. Doctoral Thesis. Rice University. 1995. 151 pages. http://hdl.handle.net/1911/19119.

Nallapareddy et al., Enterococcus faecalis adhesin, ace, mediates attachment to extracellular matrix proteins collagen type IV and laminin as well as collagen type I. Infect Immun. Sep. 2000;68(9):5218-24.

Prewett et al., Three-Dimensional Modeling of T-24 Human Bladder Carcinoma Cell Line: A New Simulated Microgravity Culture Vessel. J Tiss Cult Meth. 1993;15:29-36.

Schwarz et al., Cell Culture for Three-Dimensional Modeling in Rotating-Wall Vessels: an Application of Simulated Microgravity. J Tiss Cult Meth. 1992;14:51-8.

Simon et al., Diamagnetic Levitation: Flying Frogs and Floating Magnets. J Appl Phys. May 1, 2000;87(9):6200-4.

Simon et al., Diamagnetically stabilized magnet levitation. Am J Phys. 2001;69(6):702-13.

Suh et al., Regulation of smooth muscle cell proliferation using paclitaxel-loaded poly(ethylene oxide)-poly(lactide/glycolide) nanospheres. J Biomed Mater Res. Nov. 1998;42(2):331-8.

Tsao et al., Responses of Gravity Level Variations on the NASA/JSC Bioreactor System. Physiologist. 1992;35(1):549-50.

* cited by examiner

FERROMAGNETIC CELL AND TISSUE CULTURE MICROCARRIERS

CROSS-REFERENCE TO RELATED APPLICATIONS

This Application claims the benefit under 35 U.S.C. §120 of U.S. application Ser. No. 14/090,655, entitled "FERROMAGNETIC CELL AND TISSUE CULTURE MICROCARRIERS" filed on Nov. 26, 2013, which is herein incorporated by reference in its entirety. Application Ser. No. 14/090,655 claims the benefit under 35 U.S.C. §120 of U.S. application Ser. No. 11/307,077, filed on Jan. 23, 2006, which is herein incorporated by reference in its entirety. Application Ser. No. 11/307,077 is a continuation of International Patent Application Serial No. PCT/US2004/023746, filed Jul. 23, 2004. Application PCT/US2004/023746 claims priority under 35 U.S.C. §119(e) to U.S. Provisional Application Ser. No. 60/481,126, filed on Jul. 23, 2003, which is herein incorporated by reference in its entirety.

BACKGROUND OF THE INVENTION

It has long been established that cells and tissue growing in microgravity behave differently than those on Earth. The ongoing challenge for the experimental study of cell behavior under these conditions has been simulating the environment of microgravity so that complete laboratory studies can be conducted on Earth. This provides the obvious advantages of cost-effectiveness and safety.

To address this issue, NASA developed the bioreactor in the 1980s. Essentially, the bioreactor is a cylindrical vessel equipped with a membrane for gas exchange and ports for media exchange and sampling. As the bioreactor turns, the cells continually fall through the medium yet never hit bottom. Under these conditions, the cells form clusters that sometimes grow and differentiate much as they would in the body. Unfortunately however, on Earth the clusters become too large to fall slowly. This requires the research to be continued in the true weightlessness of space.

It has been well established that a number of cell types grow in the bioreactor on Earth for extended periods in ways that resemble tissue-like behavior. For this reason, the bioreactor provides cell culture studies with a new tool for the study of 3-dimensional cell growth and differentiation.

Bioreactors have been used aboard the Mir space station to grow larger cultures than even terrestrial Bioreactors can support. Several cancer types, including breast and colon cancer cells, have been studied in this manner. Continued research using the NASA Bioreactor is planned aboard the international Space Station.

NASA-developed tissue engineering technology has greatly facilitated advancements in the design of three-dimensional cellular constructs that exhibit many tissue-like qualities. The NASA rotating wall vessel (RWV) is a low shear, optimized suspension culture which, like a clinostat, maintains growing cellular constructs in a state of free fall via randomization of the gravity vector. Multicellular constructs are cultured under spatially unrestricted conditions during constant rotation of the vessel about its horizontal axis, resulting in time-averaging of the g vector to near zero. Significant changes in gene expression, cellular physiology and morphology occurring during three-dimensional growth in the RWV have been attributed to a variety of factors particular to this culture paradigm, including significantly reduced shear stress, altered gravitational influence (sometimes referred to as modeled or simulated microgravity), adequate mass transfer of nutrients and waste removal, and the generation of three-dimensional architecture itself. Each of these parameters is readily addressed in cell culture studies performed in the environment of space, where three-dimensional development occurs under conditions of true microgravity, fluid shear is absent and mass transfer may be controlled. In ground based studies, however, it has been difficult to separate these parameters from one another in order to examine the influence of each on three-dimensional cellular growth and function.

Therefore, what is needed is an efficacious method of simulating a microgravity environment thus allowing long-term three-dimensional (3D) development during in vitro cell and tissue culture. Commercially available magnetic beads are either too small for use as microcarriers in cell culture (diameters on the order of <10 um which are not feasible for use as cell culture supports), and/or they lack appropriate surface matrix coating to facilitate cell adherence, a requisite factor to maintain cell-cell interactions for 3D construct development during in vitro culture. Typical uses for commercially available magnetic beads are for cell and protein separation technology.

BRIEF SUMMARY OF THE INVENTION

In one embodiment of the present invention a method is provided for developing a three-dimensional cell culture model. This is accomplished by providing a plurality of microcarriers, an upper and lower graphite plate, an adjustable platform (whereby the upper and lower plate are adjustably spaced) and an upper strong magnet. Next at least one cell is adhered to the magnetic microcarriers in a gas-permeable tissue culture bag. The tissue culture bag is then placed between the upper graphite plate and the lower graphite plate, situated below the upper magnet whereby the growing cells are levitated by adjustment of the platform to the appropriate height and are held in suspension via natural magnetic forces stabilized by the graphite plates, thereby allowing the study of three-dimensional cell growth in suspension in a constant and nonrandomized environment. In another embodiment of this method the microcarriers are ferromagnetic microcarriers. The method may also be employed wherein the upper and lower graphite plates are pyrolytic graphite plates. Continued growth of the cellular constructs is made possible by placing the adjustable platform in a standard incubator.

Also provided is a microcarrier bead having a supporting surface for the attachment of cells, the microcarrier bead further comprising, at least one magnetically charged molecule and a cellular matrix material. In one embodiment the magnetically charged molecule is magnetite ($Fe_3O_4$) and the microcarrier cellular matrix material is Type I solubilized collagen. The support material may be constructed from porous gelatin.

Another embodiment includes a method of manufacturing a gelatin microcarrier bead having a supporting surface for the attachment of cells, comprising the steps of (a) swelling a porous gelatin microcarrier in culture media; (b) sterilizing the swelled microcarrier; (c) suspending the sterilized microcarriers in an acidic solution; (d) rotating the solution for a first predetermined time, at a first predetermined temperature; (e) rotating the solution for a second predetermined time, at a second predetermined temperature; and (f) stabilizing the loaded microcarriers prior to use. The gelatin microcarriers range in size from about 100-400 μM. In a preferred embodiment the culture media is void of calcium and magnesium. The ratio of microcarriers to culture media is about 0.5 g beads/25 ml media. After swelling the microcarriers are sterilized by conventional methods, as in an autoclave. The acidic solution further comprises 1 mg Type 1 solubilized collagen and 25 mg sterile fine granular magnetite ($Fe_3O_4$) and has a final volume of about 2 ml. In one embodiment the solution is then rotated at room temperature overnight, about 4 to 8 hours. Next the solution is rotated at about 37 degrees Celsius for about 24 to 48 hours.

The stabilizing step of the abovementioned embodiment further comprises the steps of (a) washing the microcarriers to remove any excess collagen and magnetite ($Fe_3O_4$) and (b) storing the microcarriers in a protein-containing media at a neutral pH under sterile conditions at 4 degrees Celsius.

Another embodiment of the present invention provides a method of manufacturing an alginate microcarrier bead having a supporting surface for the attachment of cells, comprising the steps of (a) providing a solution comprising alginate and culture media lacking calcium and magnesium, (b) adding sterile fine granular magnetite ($Fe_3O_4$) to the solution, (c) expressing the combined solution in droplet form into a solution of calcium chloride wherein the microcarrier bead is formed in about 1-2 hours, (d) washing the microcarrier beads with culture media; and (e) coating the microcarrier beads with a collagen solution. In this embodiment the solution comprising alginate and culture media lacking calcium and magnesium contains about 2% alginate (about 0.5 g alginate per 25 ml). The amount of sterile fine granular magnetite ($Fe_3O_4$) used is about 150 mg. The solution of calcium chloride is about 25 mM calcium chloride and the collagen solution is about 0.3 mg solubilized Type I collagen.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE INVENTION

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Figure 1:
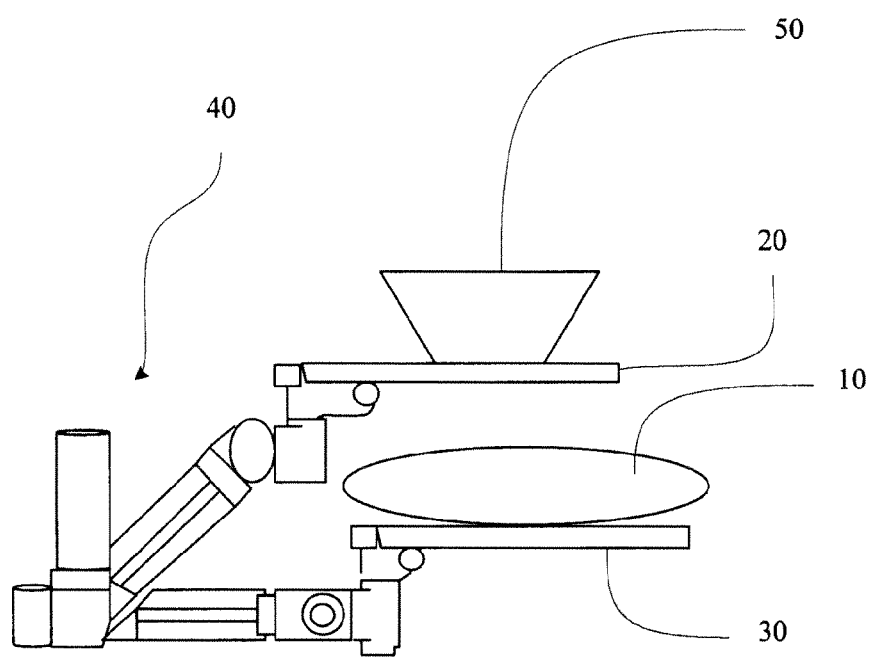
FIG. 1 is a side elevational view of the inventive method, wherein a gas-permeable tissue culture bag is placed on an adjustable platform.

In an effort to dissect the influence of fluid shear and randomized gravity from three-dimensional development, one embodiment of the present invention, shown in FIG. 1, applies the concept of diamagnetically stabilized levitation to develop a new type of three-dimensional cell culture model. Cells are adhered to ferromagnetic microcarriers within gas-permeable tissue culture bags 10. The bags are placed between an upper 20 and lower 30 pyrolytic graphite plate on an adjustable lifter platform 40, under the influence of a strong NdFeB magnet 50 located above the upper graphite plate. The growing constructs are levitated by adjustment of the platform to the appropriate height, and the apparatus is placed into a standard incubator. The unit requires no source of electrical power, since the growing cellular constructs are held in suspension via natural magnetic forces stabilized by diamagnetic (repelling) plates, thereby allowing the study of three-dimensional cell growth in suspension in a constant and nonrandomized 1 g environment. Because the constructs remain fixed in position, this configuration also replicates the mass transfer conditions inherent in undisturbed cell culture in the true microgravity of space where mass transfer is limited to simple diffusion; a perfusion model is under development in order to impart control of mass transfer conditions to this culture system. Controlled introduction of fluid shear may be accomplished in two ways: placement of the apparatus on an orbiting platform or by rotation of the upper magnet to induce spin of the cellular constructs within the culture bag.

The presence of a magnetic field during three-dimensional cell culture obviously introduces a variable with the potential to influence cell growth, the effects of which have yet to be fully investigated in this system. However, this technique affords a unique opportunity to examine mechanisms by which natural magnetic fields may influence multicellular construct growth and physiology, and associated changes in gene expression—both in the absence and presence of other physical parameters known to affect cell function, such as fluid shear and mass transfer. Studies performed thus far demonstrate several positive growth effects in this system, including rapid adherence to the microcarrier surface and multilayered outgrowth resulting in the generation of large-sized constructs on the order of 1 cm in diameter.

Another embodiment of the invention is a ferromagnetic microcarrier bead for in vitro cell and tissue. The invention describes methodology for creating the beads which have inserted within them magnetite ($Fe_3O_4$) in the presence of cellular matrix material such as collagen. Cells grown on these microcarriers readily form complex multicellular, tissue-like 3D constructs when cultured in a spatially unrestricted environment using the principle of diagmagnetic levitation, that is, the use of magnetic, paramagnetic, ferromagnetic and diamagnetic (repelling) fields to create a suspension culture capable of sustained, stable levitation. It is also envisioned that these ferromagnetic microcarriers may find application in standard in vitro tissue culture, wherein following enzymatic release of single cells and/or multicellular constructs from the microcarrier surface, the microcarriers are very easily removed from the cell suspension via a removal magnet. It is further envisioned that the magnetite could also be incorporated into the microcarriers in the presence of biodegradable encapsulated drug, for use in magnetically guided drug delivery to a specific site or target tissue.

The beads described above are porous, collagen coated, ferromagnetic cell culture microcarriers, which are suitable for in vitro cell and tissue culture and which facilitate 3D multicellular construct generation. The invention describes a method for creating batches of microcarriers which have inserted within them magnetite (Fe3O4) in the presence of collagen, thus creating a microcarrier which becomes magnetic in nature when placed in a the presence of a magnetic field and which facilitates cellular adherence (via the collagen coating) for 3D construct development.

The cells grown on these ferromagnetic microcarriers readily form complex, multicellular, tissue-like 3D constructs when cultured in a spatially unrestricted environment using the principle of diagmagnetic levitation, that is, the use of magnetic, paramagnetic, ferromagnetic and diagmagnetic (repelling) fields to create a suspension culture capable sustained, stable levitation. Although it is typically desirable for most microcarriers to have density close to 1.0 g/cm3 (e.g., near the density of standard culture media) in order to facilitate neutral buoyancy, the density of the microcarriers described herein is not of consequence for diagmagnetic levitation, since they are held in suspension via magnetic fields. The multicellular constructs generated may be useful for the creation of bioengineered tissue (for human and veterinary purposes), and for research purposes to understand mechanisms of cell growth and disease formation. These ferromagnetic microcarriers may also be of use in standard in vitro cell culture, wherein following enzymatic release of single cells and/or multicellular constructs from the microcarrier surface, the microcarriers are very easily removed from the cell suspension via a removal magnet. Moreover, it is also envisioned that the magnetite could be incorporated into the microcarriers in the presence of biodegradable nanospheres of encapsulated drug. Through the use of a guiding magnetic field, these magnetite/drug loaded microbeads could be directed to allow for magnetically directed drug delivery to a specific site or tissue. Finally, based upon their distinct striped appearance, these microcarriers have been named "Tiger Beads".

Protocol for Creating Ferromagnetic Gelatin Microcarriers

Figure 2:
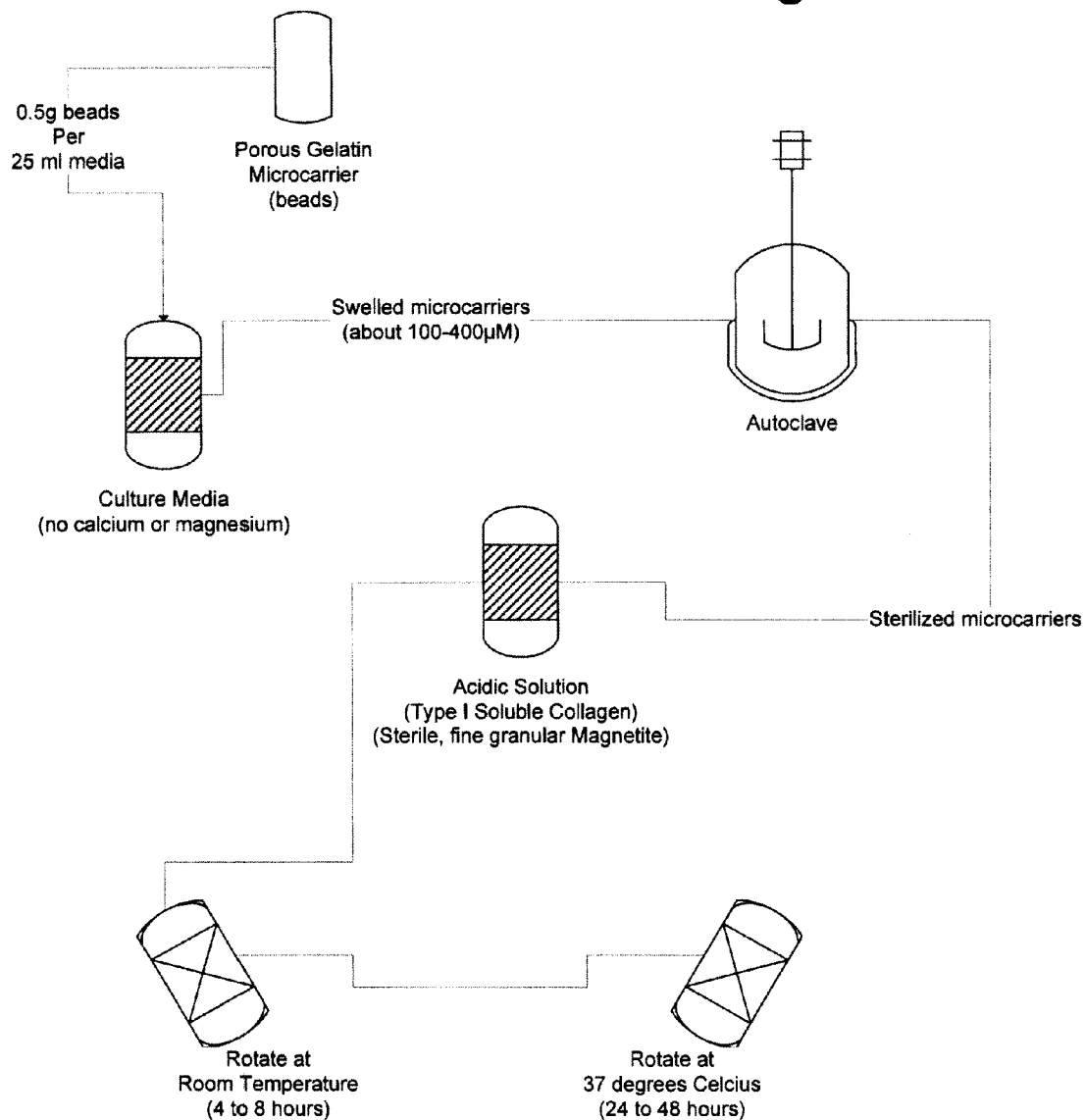
FIG. 2 is a flowchart outlining the protocol for creating ferromagnetic gelatin microcarriers.

Referring now to FIG. 2, porous cross linked gelatin microcarriers 10 of a size range of 100-400 µM are swelled in culture media lacking calcium and magnesium (0.5 g beads/25 ml media) after which they are sterilized by autoclaving 20. In step 3, (represented by the numeral 30) the sterile cross-linked gelatin microcarriers (20 mg) are placed into an acidic suspension containing 1 mg type I solubilized collagen and 25 mg sterile fine granular magnetite ($Fe_3O_4$); the final volume is approximately 2 ml. The suspension is rotated at room temperature 40 overnight then rotated at 37° C. for an additional 24-48 hours 50 until visible evidence of magnetite incorporation is noted. The incorporation of magnetite into the microcarriers is readily observable using a dissecting or inverted phase contrast microscope at low magnification. Afterwards, the microcarrier suspension is washed to remove collagen and excess (unincorporated) magnetite, and stored under sterile conditions at 4° C. in a high protein-containing media (such as standard cell culture media with 20% serum added) at neutral pH, to stabilize the magnetite-loaded microcarriers prior to use in cell culture.

Protocol for Creating Ferromagnetic Alginate Microcarriers

Figure 3:
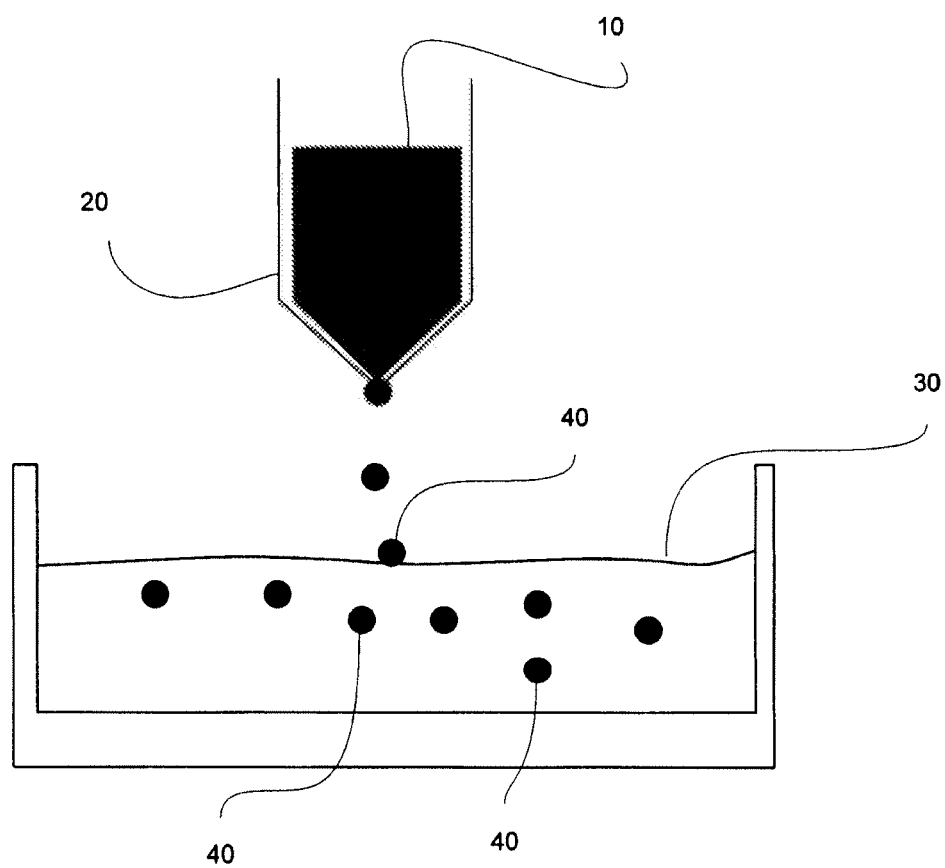
FIG. 3 is a diagrammatic representation of the protocol for creating ferromagnetic alginate microcarriers.
Figure 4:
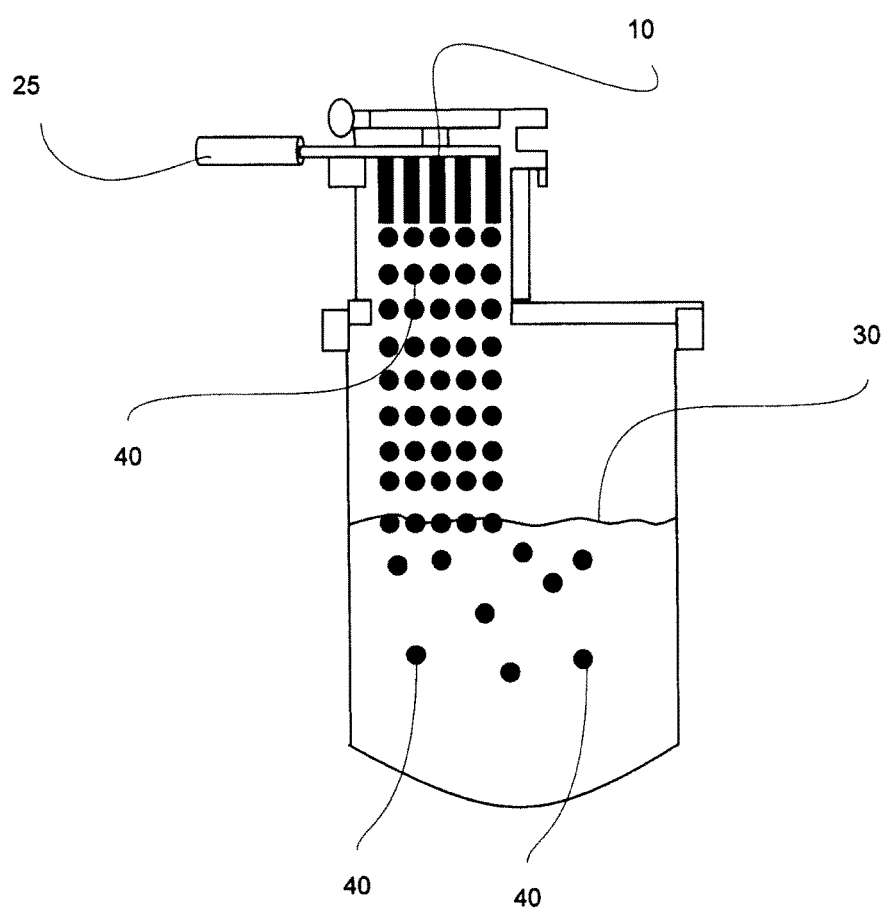
FIG. 4 is a diagrammatic representation of an alternative protocol for creating ferromagnetic alginate microcarriers.

Referring now to FIG. 3, a 2% solution of alginate (0.5 g alginate per 25 ml) 10 is prepared using culture media lacking calcium and magnesium to which is added 150 mg of sterile fine granular magnetite ($Fe_3O_4$). The solution is slowly expressed in droplet form from the tip of a tuberculin syringe 20 or via fine mechanized spray (25, FIG. 4) into a solution of 25 mM calcium chloride 30. The beads 40 formed are allowed to gel for 1-2 hours and then washed with culture media after which they are coated overnight with a solution of 0.3 mg solubilized type I collagen.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be be the to fall therebetween. Now that the invention has been described,

I claim:

1. A method of studying three-dimensional cell growth, comprising the steps of:
    providing a plurality of microcarriers, wherein the microcarriers are magnetic microcarriers;
    providing an upper and a lower diamagnetic plate;
    providing an adjustable platform, whereby the upper and lower diamagnetic plates are adjustably spaced;
    adhering at least one cell to the microcarriers in a gas-permeable tissue culture bag;
    placing the tissue culture bag between the upper diamagnetic plate and the lower diamagnetic plate; and
    placing a magnet above the upper diamagnetic plate relative to the tissue culture bag whereby the growing cells are levitated by adjustment of the platform to the appropriate height and are held in suspension via natural magnetic forces stabilized by the diamagnetic plates, thereby allowing the study of three-dimensional cell growth in suspension in a constant and nonrandomized environment.

2. The method of claim 1, wherein the microcarriers are ferromagnetic microcarriers.

3. The method of claim 1, wherein the upper and lower diamagnetic plates are graphite plates.

4. The method of claim 1, wherein the adjustable platform is placed in an incubator.

5. The method of claim 1, wherein the plurality of microcarriers include microcarrier beads having a supporting surface for the attachment of cells, the microcarrier beads further comprising: at least one magnetically charged molecule; and a cellular matrix material.

6. The method of claim 5, wherein the magnetically charged molecule is magnetite (Fe3O 4).

7. The method of claim 5, wherein the cellular matrix material is Type I solubilized collagen.

8. The method of claim 5, wherein the supporting surface comprises a porous gelatin.

9. The method of claim 3, wherein the graphite plates are pyrolytic graphite plates.

10. The method of claim 1, further comprising rotating the magnet relative to the tissue culture bag.

11. A method comprising the steps of:
    placing a container between first and second diamagnetic plates and proximate to at least one magnet, wherein the container contains a plurality of microcarriers and at least one cell adhered to the plurality of microcarriers, wherein the plurality of microcarriers are magnetic microcarriers; and
    adjusting a height of the magnet relative to the container such that the plurality of microcarriers are levitated in suspension via natural magnetic forces and stabilized by the diamagnetic plates.

12. The method of claim 11, wherein adjusting the height of the magnet relative to the container further comprises adjusting a height of the magnet and the first diamagnetic plate relative to the container simultaneously.

13. The method of claim 12, wherein adjusting the height of the magnet and the first diamagnetic plate further comprises adjusting the height of a platform associated with the magnet and the first diamagnetic plate relative to the container.

14. The method of claim 11, further comprising placing the platform in an incubator.

15. The method of claim 11, wherein the container is a gas-permeable tissue culture bag.

16. The method of claim 11, wherein the microcarriers are ferromagnetic microcarriers.

17. The method of claim 11, the first and second diamagnetic plates are graphite plates.

18. The method of claim 17, wherein the graphite plates are pyrolytic graphite plates.

19. The method of claim 11, wherein the plurality of microcarriers include microcarrier beads having a supporting surface for the attachment of cells, the microcarrier beads further comprising: at least one magnetically charged molecule; and a cellular matrix material.

20. The method of claim 19, wherein the magnetically charged molecule is magnetite ($Fe_3O_4$).

21. The method of claim 19, wherein the cellular matrix material is Type I solubilized collagen.

22. The method of claim 19, wherein the supporting surface comprises a porous gelatin.

23. The method of claim 11, further comprising rotating the magnet relative to the tissue culture bag.

\* \* \* \* \*